(12) United States Patent
Nishigishi

(10) Patent No.: US 9,427,345 B2
(45) Date of Patent: Aug. 30, 2016

(54) PUSHER GUIDE WIRE

(71) Applicant: ASAHI INTECC CO., LTD., Nagoya-shi, Aichi (JP)

(72) Inventor: Makoto Nishigishi, Owariasahi (JP)

(73) Assignee: ASAHI INTECC CO., LTD., Nagoya-shi (JP)

( * ) Notice: Subject to any disclaimer, the term of this patent is extended or adjusted under 35 U.S.C. 154(b) by 0 days.

(21) Appl. No.: 14/100,697

(22) Filed: Dec. 9, 2013

(65) Prior Publication Data

US 2014/0324148 A1   Oct. 30, 2014

(30) Foreign Application Priority Data

Apr. 30, 2013   (JP) ................................. 2013-095282

(51) Int. Cl.
| | |
|---|---|
| *A61F 2/06* | (2013.01) |
| *A61F 2/95* | (2013.01) |
| *A61F 2/962* | (2013.01) |
| *A61F 2/966* | (2013.01) |

(52) U.S. Cl.
CPC ................ *A61F 2/95* (2013.01); *A61F 2/966* (2013.01); *A61F 2/962* (2013.01); *A61F 2002/9665* (2013.01); *A61F 2220/0033* (2013.01)

(58) Field of Classification Search
CPC .......... A61F 2/966; A61F 2/95; A61F 2/962; A61F 2002/9665; A61F 2220/0033
USPC ....................... 623/1.11, 1.12, 1.23; 606/108
See application file for complete search history.

(56) References Cited

U.S. PATENT DOCUMENTS

| 6,955,685 | B2 | 10/2005 | Escamilla et al. | |
|---|---|---|---|---|
| 7,001,422 | B2 | 2/2006 | Escamilla et al. | |
| 7,309,351 | B2 | 12/2007 | Escamilla et al. | |
| 2002/0016597 | A1* | 2/2002 | Dwyer | A61F 2/95 606/108 |
| 2002/0045929 | A1* | 4/2002 | Diaz | A61F 2/95 623/1.11 |
| 2004/0049204 | A1* | 3/2004 | Harari | A61F 2/958 606/108 |
| 2006/0089703 | A1 | 4/2006 | Escamilla et al. | |
| 2006/0095213 | A1 | 5/2006 | Escamilla et al. | |
| 2006/0271149 | A1* | 11/2006 | Berez | A61B 17/12022 623/1.11 |
| 2007/0198076 | A1* | 8/2007 | Hebert | A61F 2/962 623/1.11 |
| 2008/0255654 | A1* | 10/2008 | Hebert | A61F 2/95 623/1.11 |

(Continued)

FOREIGN PATENT DOCUMENTS

| JP | B2-4498709 | 7/2010 |
|---|---|---|
| WO | 01/54614 A2 | 8/2001 |
| WO | 02/056798 A2 | 7/2002 |

OTHER PUBLICATIONS

Jul. 28, 2015 Office Action issued in Japanese Patent Application No. 2013-095282.

(Continued)

*Primary Examiner* — Jing Ou
(74) *Attorney, Agent, or Firm* — Oliff PLC

(57) ABSTRACT

In a pusher guide wire, a protective film is suspended with respect to a core shaft with a distal end thereof being fitted in a distal-end holder and a proximal end thereof being fitted in a proximal-end holder. Hence, the frictional resistance generated between the protective film and a stent when the core shaft is rotated is reduced. Thus, the protective film is prevented from coming off the core shaft, the stent is prevented from being damaged, and the transmissibility of rotation of the pusher guide wire is improved. Consequently, the position where the stent is to be released is easily adjustable.

18 Claims, 5 Drawing Sheets

(56) References Cited

U.S. PATENT DOCUMENTS

2008/0300667 A1* 12/2008 Hebert ............... A61F 2/95 623/1.11
2009/0264978 A1* 10/2009 Dieck ............... A61F 2/95 623/1.11
2011/0301685 A1 12/2011 Kao

OTHER PUBLICATIONS

May 3, 2016 Extended European Search Report issued in European Patent Application No. 14153160.8.

* cited by examiner

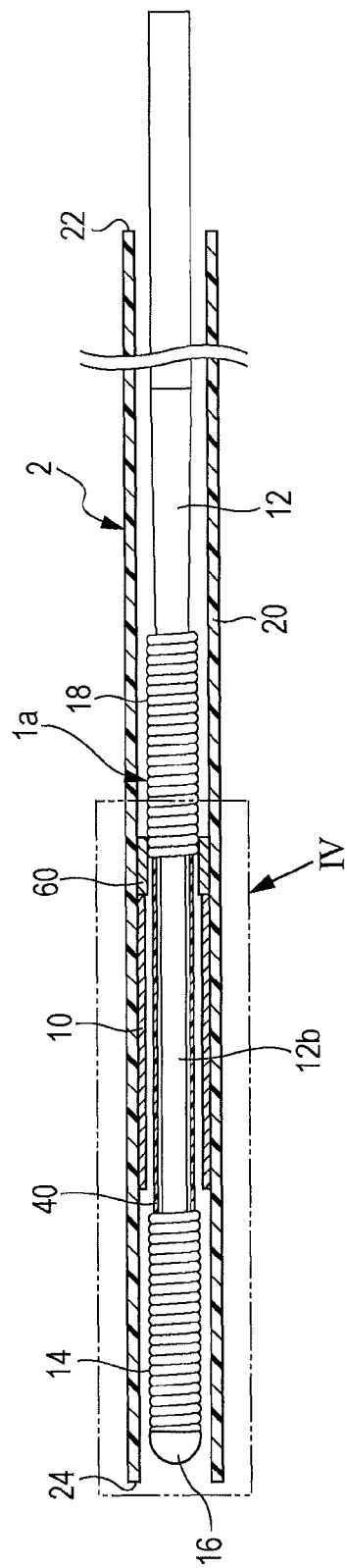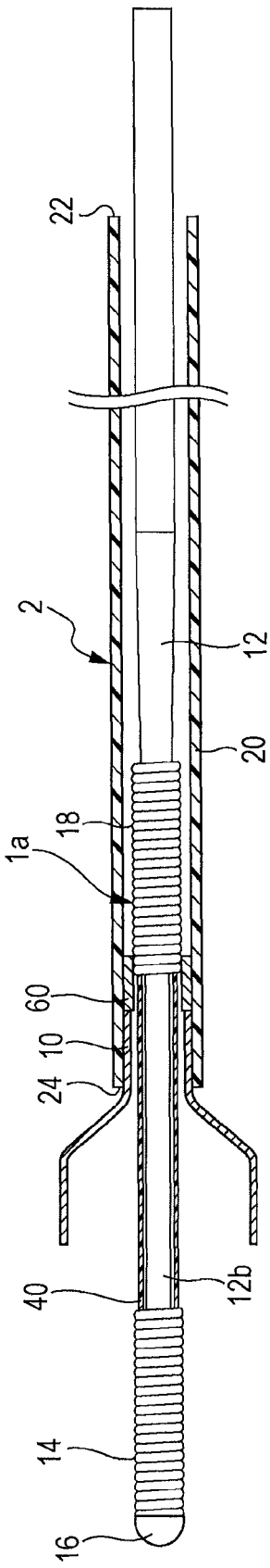

PUSHER GUIDE WIRE

CROSS-REFERENCE TO RELATED APPLICATION

The present application claims priority to Japanese Patent Application No. 2013-095282 filed in the Japan Patent Office on Apr. 30, 2013, the entire contents of which are incorporated herein by reference.

BACKGROUND

The disclosed embodiments relate to a medical device. Specifically, the disclosed embodiments relate to a pusher guide wire that delivers a stent contained in a catheter to a target site.

A stent is a medical instrument that supports the lumen of a blood vessel or a digestive organ so that the blood vessel or the digestive organ that has been temporarily expanded by a balloon catheter or the like does not constrict again. There are different types of stents which are roughly classified as balloon-expanding stents that are each expanded by a balloon catheter or the like and self-expanding stents that each naturally expand by itself. Recently, self-expanding stents that do not tend to deform by external forces have been in frequent use.

In a related-art method of delivering a self-expanding stent to a target site (see Japanese Patent No. 4498709, for example), while the stent that is provided around a pusher guide wire is contained in a distal-end portion of a catheter, the catheter is made to advance up to a target site. Subsequently, the pusher guide wire is pushed toward the distal end of the catheter. Thus, the stent is delivered from the distal end of the catheter to the target site. In the pusher guide wire disclosed by Japanese Patent No. 4498709, the stent is provided between a distal-end coil member functioning as a distal-end stopper and a proximal-end coil member functioning as a proximal-end stopper, and a resin protective film is provided between the stent and a core shaft so as to prevent the stent from coming into contact with the core shaft of the pusher guide wire.

In the above pusher guide wire, the protective film is fixed to the core shaft and is not suspended with respect thereto. Hence, when the core shaft is rotated, the protective film also rotates. Thus, when the core shaft is rotated, a frictional resistance is generated between the protective film and the stent, resulting in damage to the stent or failure in the transmission of rotation of the core shaft to the distal end of the pusher guide wire (i.e., poor transmissibility of rotation of the pusher guide wire) because of the frictional resistance generated between the protective film and the stent.

SUMMARY

In view of the above problems, the disclosed embodiments provide a pusher guide wire in which a protective film does not tend to rotate together with a core shaft when the core shaft is rotated, whereby the protective film is prevented from coming off the core shaft and a stent is prevented from being damaged while the rotation of the core shaft is transmitted to the distal end of the pusher guide wire.

The above problems are to be solved by the following.

According to some aspects of the invention, there is provided a pusher guide wire having a pusher portion that delivers a stent to a target site. The pusher guide wire includes a core shaft, a protective film that is provided around a portion of the core shaft and that is slidable in a longitudinal direction of the core shaft, a distal-end holder (or recessed portion) joined to the core shaft, the distal-end holder preventing the protective film from moving toward a distal-end, and a proximal-end holder (or recessed portion) joined to the core shaft, the proximal-end holder preventing the protective film from moving toward a proximal-end. A distal end of the protective film is covered by the distal-end holder, and a proximal end of the protective film is covered by the proximal-end holder.

In the pusher guide wire according to some aspects of the invention, the distal end of the protective film is covered by the distal-end holder, and the proximal end of the protective film is covered by the proximal-end holder. Therefore, the protective film is suspended with respect to the core shaft without coming off of the core shaft and does not tend to rotate together with the core shaft when the core shaft is rotated. Consequently, the frictional resistance generated between the protective film and the stent when the core shaft is rotated is reduced, and the probability that the stent may be damaged or that the rotation of the core shaft might not be transmitted to the distal end of the pusher guide wire is reduced.

BRIEF DESCRIPTION OF THE DRAWINGS

FIG. 3A illustrates the entirety of a pusher guide wire according to a second embodiment, which differs from the pusher guide wire illustrated in FIGS. 1A and 1B, with the stent being in the catheter.

FIG. 3B illustrates a state where the stent is being released from the catheter.

DETAILED DESCRIPTION OF EMBODIMENTS

Figure 1A:
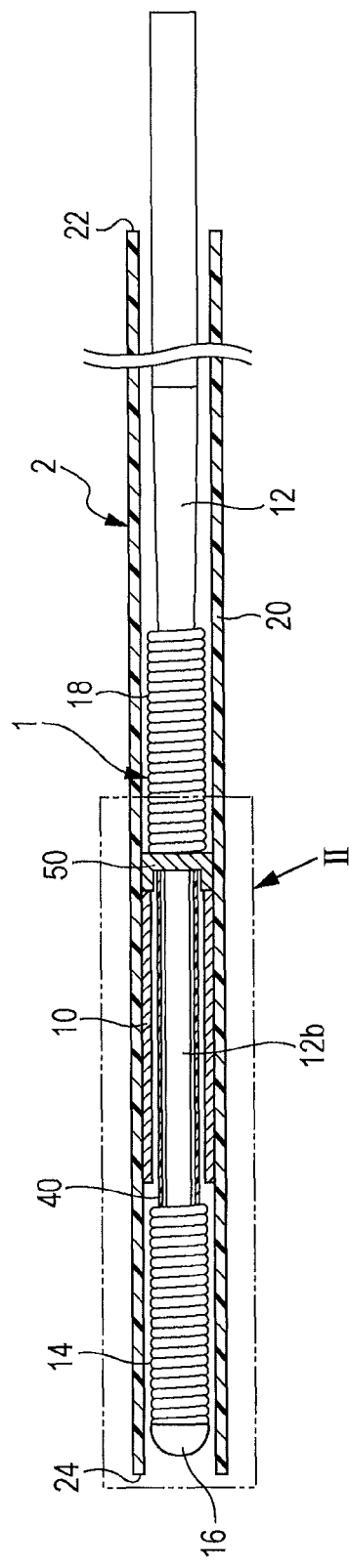
FIG. 1A illustrates the entirety of a pusher guide wire according to a first embodiment that delivers a stent contained in a catheter to a target site, with the stent being in the catheter.
Figure 1B:
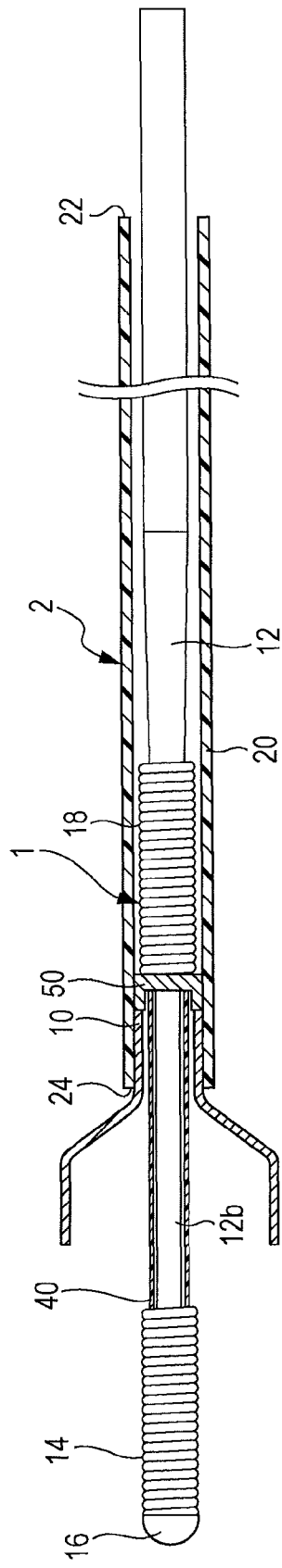
FIG. 1B illustrates a state where the stent is being released from the catheter.
Figure 2:
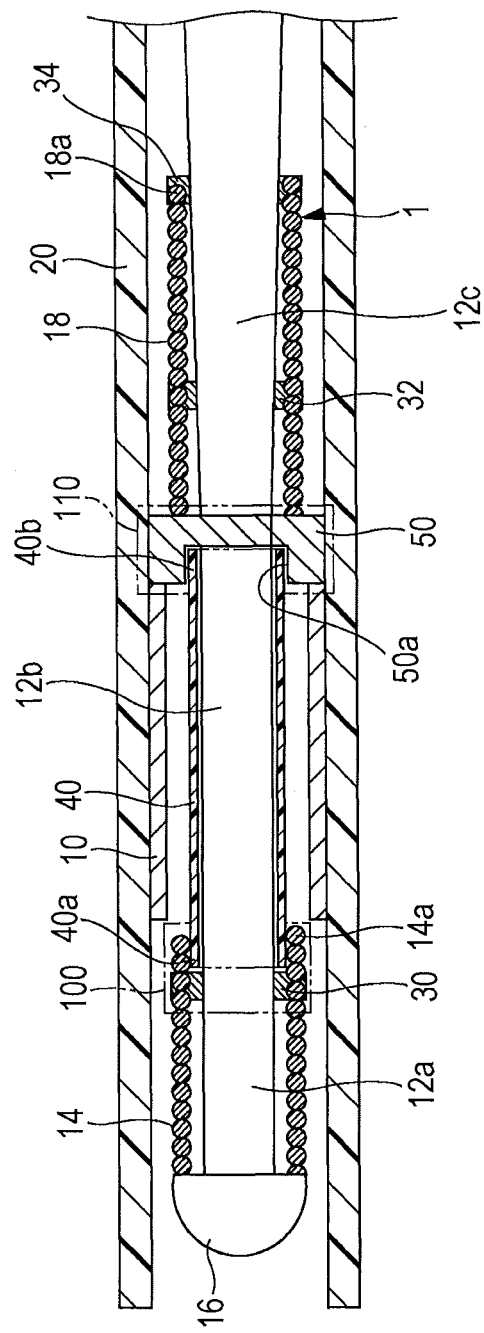
FIG. 2 is an enlarged sectional view of part II illustrated in FIG. 1A.

Referring to FIGS. 1A to 2, a pusher guide wire 1 according to a first embodiment will now be described. In FIGS. 1A to 2, the left side corresponds to a distal-end (far side) that is to be inserted into a human body, and the right side corresponds to a proximal-end (near side) that is to be operated by an operator such as a doctor. FIG. 2 is an enlarged sectional view of part II illustrated in FIG. 1A.

As illustrated in FIGS. 1A, 1B, and 2, the pusher guide wire 1 is configured to deliver a stent 10 to a target site and includes a core shaft 12, a distal-end coil member 14 wound around a first distal-end portion 12a of the core shaft 12, a distal-end tip 16 joining the distal end of the core shaft 12 and the distal end of the distal-end coil member 14 to each other, and a proximal-end coil member 18 that is provided proximally (the right side in the drawings) of the distal-end coil member 14 and that is wound around a third distal-end portion 12c of the core shaft 12. For the convenience of description, the core shaft 12 is herein sectioned into the first distal-end portion 12a covered by the distal-end coil member 14, the third distal-end portion 12c covered by the proximal-end coil member 18, and a second distal-end portion 12b provided between the first distal-end portion 12a and the third distal-end portion 12c.

A catheter 2 has a cylindrical body 20 into which the pusher guide wire 1 is insertable. The pusher guide wire 1, in which the stent 10 is provided between the distal-end coil member 14 and the proximal-end coil member 18, is insertable into the catheter 2 from a proximal-end inlet 22 of the catheter 2. The catheter 2 may be any of known catheters, and a description thereof is omitted.

Referring to FIG. 2, a joining member 30 (such as a solder material) joins the distal-end coil member 14 and the first distal-end portion 12a of the core shaft 12 to each other. A joining member 32 (such as a solder material) joins the proximal-end coil member 18 and the third distal-end portion 12c of the core shaft 12 to each other. A joining member 34 (such as a solder material) joins a proximal end 18a of the proximal-end coil member 18 and the third distal-end portion 12c of the core shaft 12 to each other.

A protective film 40 made of resin is provided between the stent 10 and the second distal-end portion 12b of the core shaft 12. The protective film 40 covers the second distal-end portion 12b of the core shaft 12 but is not fixed to the second distal-end portion 12b of the core shaft 12. The protective film 40 is slidable in a longitudinal direction of the core shaft 12. Hence, as to be described below, the protective film 40 does not tend to rotate together with the core shaft 12 when the core shaft 12 is rotated.

A distal end 40a of the protective film 40 is fitted between a proximal-end portion 14a of the distal-end coil member 14 and the first distal-end portion 12a of the core shaft 12. The joining member 30 prevents the protective film 40 from moving toward the distal-end (the left side in the drawings). That is, the joining member 30 functions as a distal-end stopper for the protective film 40.

A proximal-end stopper 50 that is joined to the second distal-end portion 12b of the core shaft 12 is provided between the stent 10 and the proximal-end coil member 18. The proximal-end stopper 50 includes a recessed portion 50a provided by cutting off a part of a cylindrical body thereof. A proximal end 40b of the protective film 40 is fitted in the recessed portion 50a of the proximal-end stopper 50, whereby the protective film 40 is prevented from moving toward the proximal end (the right side in the drawings). The proximal-end stopper 50 also functions as a pusher portion that pushes the stent 10 toward the distal end (the left side in the drawings).

The distal end 40a of the protective film 40 is fitted in a distal-end recessed portion 100 that is formed of the proximal-end portion 14a of the distal-end coil member 14 and the joining member 30 functioning as a distal-end stopper. The distal-end coil member 14 extends from the distal-end tip 16 to a position located proximally of the distal end 40a of the protective film 40. Meanwhile, the proximal end 40b of the protective film 40 is fitted in a proximal-end recessed portion 110 that is formed of the recessed portion 50a of the proximal-end stopper 50. That is, the protective film 40 is provided around the second distal-end portion 12b of the core shaft 12 with the distal end 40a thereof being covered by the distal-end recessed portion 100 and the proximal end 40b thereof being covered by the proximal-end recessed portion 110.

As illustrated in FIGS. 1A and 1B, when the core shaft 12 is pushed toward the distal-end (the left side in the drawings) with the stent 10 being in the distal-end portion of the catheter 2 (as illustrated in FIG. 1A), the stent 10 is made to advance toward the distal-end (the left side in the drawings) by the proximal-end stopper 50 that is joined to the core shaft 12. Consequently, the stent 10 is released from a distal-end outlet 24 of the catheter 2 toward the target site (as illustrated in FIG. 1B).

To release the stent 10 toward the target site, the operator not only pushes the core shaft 12 toward the distal-end (the left side in the drawings) but also rotates the core shaft 12 in some cases. For example, if the target site is in a curved peripheral blood vessel, the distal-end portion of the catheter 2 is bent. Therefore, even if the core shaft 12 is pushed toward the distal-end (the left side in the drawings), the stent 10 might not advance toward the distal-end (the left side in the drawings) and might not be released from the distal-end outlet 24 of the catheter 2. In another case, even if the catheter 2 that has been temporarily retracted toward the proximal-end (the right side in the drawings) during the operation is pushed again toward the distal-end (the left side in the drawings) so that the distal-end outlet 24 of the catheter 2 is positioned at the target site, the distal-end portion of the catheter 2 might be bent and might not advance.

In the pusher guide wire 1 according to the first embodiment, when the operator rotates the core shaft 12, the protective film 40 does not tend to rotate together with the core shaft 12 because the protective film 40 is suspended with respect to the second distal-end portion 12b of the core shaft 12. Therefore, even if the core shaft 12 is rotated, the frictional resistance generated between the protective film 40 and the stent 10 is small, preventing damage to the stent 10. Moreover, since the rotation of the core shaft 12 is transmitted to the distal-end tip 16 via the joining member 30 functioning as a distal-end stopper and the distal-end coil member 14, the transmissibility of rotation of the pusher guide wire 1 is improved even if the distal-end portion of the catheter 2 is bent. Consequently, the stent 10 can be easily released from the distal-end outlet 24 of the catheter 2.

In the pusher guide wire 1, the distal end 40a of the protective film 40 is covered by the proximal-end portion 14a of the distal-end coil member 14, which has elasticity. Therefore, even if the pusher guide wire 1 is bent along a curved blood vessel or digestive organ, the proximal-end portion 14a of the distal-end coil member 14 can stretch to some extent. Hence, the probability that the protective film 40 may come out of the distal-end recessed portion 100 is reduced.

In the pusher guide wire 1, the proximal-end recessed portion 110 functions as a pusher portion that delivers the stent 10 to the target site. That is, the proximal-end recessed portion 110 has both a function of preventing the protective film 40 from coming off of the second distal-end portion 12b of the core shaft 12 and a function as a pusher portion that delivers the stent 10 to the target site. Hence, there is no need to provide a pusher portion separately from the proximal-end recessed portion 110, simplifying the manufacturing of the pusher guide wire 1.

Materials of the elements included in the pusher guide wire 1 according to the first embodiment will now be described. The materials are not limited to those described below.

The core shaft 12 may be made of stainless steel (SUS304, SUS316, or the like) or superelastic alloy such as a Ni—Ti alloy.

The distal-end coil member 14 and the proximal-end coil member 18 may each be formed of radiopaque wire that is made of, for example, gold, platinum, tungsten, or an alloy containing any of the foregoing elements. Employing the distal-end coil member 14 and the proximal-end coil member 18 that are each made of radiopaque wire enables the operator to identify the positions of the distal-end coil member 14 and the proximal-end coil member 18 in a radiographic image.

The distal-end coil member 14 and the proximal-end coil member 18 may each be formed of either a solid wire including a single piece of wire or a stranded wire including a plurality of pieces of wire. A stranded wire is superior to a solid wire in characteristics such as flexibility and restorability. Hence, the distal-end coil member 14 and the proximal-end coil member 18 are each preferably made of a stranded wire.

The distal-end tip 16 may be made of a radiopaque material such as gold, platinum, tungsten, or an alloy containing any of the foregoing elements so that the position of the distal end of the pusher guide wire 1 can be identified in a radiographic image.

The joining members 30, 32, and 34 may each be made of solder (such as aluminum alloy solder, silver solder, or gold solder), metal solder (such as an Au—Sn alloy), or the like.

The protective film 40 may be made of resin such as polyimide or fluorine-based resin.

The proximal-end stopper 50 may be made of stainless steel (SUS304, SUS316, or the like) or a superelastic alloy such as a Ni—Ti alloy, as with the core shaft 12.

Figure 4:
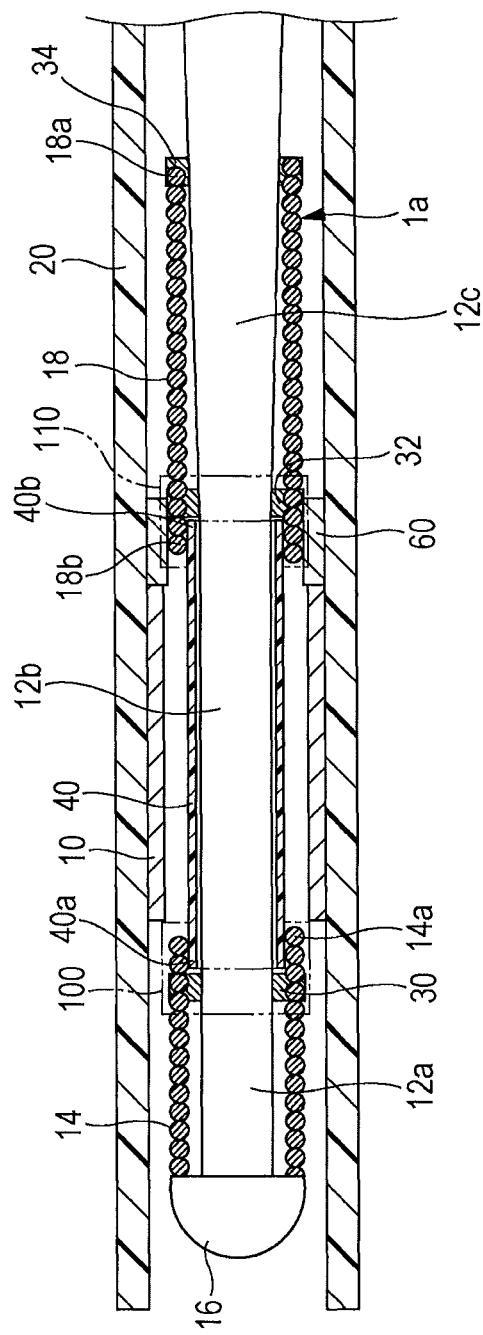
FIG. 4 is an enlarged sectional view of part IV illustrated in FIG. 3A.

Referring now to FIGS. 3A to 4, a pusher guide wire 1*a* according to a second embodiment will be described. In FIGS. 3A to 4, as in FIGS. 1A to 2, the left side corresponds to a distal-end (far side) that is to be inserted into a human body, and the right side corresponds to a proximal-end (near side) that is to be operated by an operator such as a doctor. FIG. 4 is an enlarged sectional view of part IV illustrated in FIG. 3A.

Herein, differences from the pusher guide wire 1 illustrated in FIGS. 1A to 2 will only be described. In the pusher guide wire 1*a*, the proximal end 40*b* of the protective film 40 is fitted between a distal-end portion 18*b* of the proximal-end coil member 18 and the third distal-end portion 12*c* of the core shaft 12. The proximal-end coil member 18 extends from a position located proximally of the proximal end 40*b* of the protective film 40 to a position located distally of the proximal end 40*b* of the protective film 40. The joining member 32 prevents the proximal end 40*b* of the protective film 40 from moving toward the proximal-end (the right side in the drawings) (see FIG. 4). That is, the joining member 32 functions as a proximal-end stopper for the protective film 40. Thus, the proximal end 40*b* of the protective film 40 is fitted in the proximal-end recessed portion 110 that is formed of the distal-end portion 18*b* of the proximal-end coil member 18 and the joining member 32 functioning as a proximal-end stopper. The proximal-end coil member 18 extends from a position located proximally of the proximal end 40*b* of the protective film 40 to a position located distally of the proximal end 40*b* of the protective film 40. Furthermore, in the pusher guide wire 1*a*, a pusher portion 60 that pushes the stent 10 toward the distal-end (the left side in the drawings) is joined to the distal-end portion 18*b* of the proximal-end coil member 18 in such a manner as to cover the distal-end portion 18*b*.

As described above, the distal end 40*a* of the protective film 40 is fitted in the distal-end recessed portion 100 that is formed of the proximal-end portion 14*a* of the distal-end coil member 14 and the joining member 30 that functions as a distal-end stopper. The distal-end coil member 14 extends from the distal-end tip 16 to a position located proximally of the distal end 40*a* of the protective film 40. Meanwhile, the proximal end 40*b* of the protective film 40 is fitted in the proximal-end recessed portion 110 that is formed of the distal-end portion 18*b* of the proximal-end coil member 18 and the joining member 32 that functions as a proximal-end stopper. The proximal-end coil member 18 extends from a position located proximally of the proximal end 40*b* of the protective film 40 to a position located distally of the proximal end 40*b* of the protective film 40. Therefore, in the pusher guide wire 1*a*, as in the pusher guide wire 1, the protective film 40 is provided around the second distal-end portion 12*b* of the core shaft 12 with the distal end 40*a* thereof being covered by the distal-end recessed portion 100 and the proximal end 40*b* thereof being covered by the proximal-end recessed portion 110.

In the pusher guide wire 1*a*, the distal end 40*a* and the proximal end 40*b* of the protective film 40 are covered by the proximal-end portion 14*a* of the distal-end coil member 14 and the distal-end portion 18*b* of the proximal-end coil member 18, which both have elasticity. Therefore, even if the pusher guide wire 1 is bent along a curved blood vessel or digestive organ, the proximal-end portion 14*a* of the distal-end coil member 14 and the distal-end portion 18*b* of the proximal-end coil member 18 can stretch to some extent. Hence, the probability that the protective film 40 may come out of the distal-end recessed portion 100 and the proximal-end recessed portion 110 is reduced.

Figure 5:
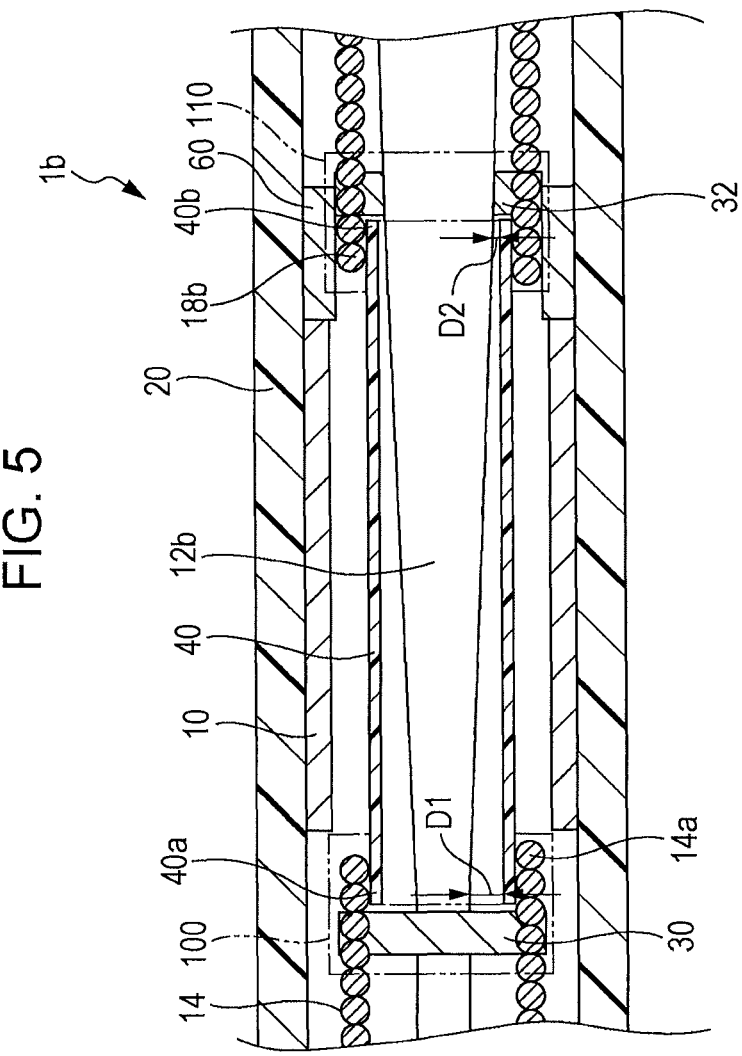
FIG. 5 illustrates a modification of the pusher guide wire illustrated in FIG. 4.

Referring now to FIG. 5, a pusher guide wire 1*b* according to a third embodiment, which is a modification of the second embodiment illustrated in FIG. 4, will be described, focusing only on differences from the pusher guide wire 1*a* illustrated in FIG. 4. In the pusher guide wire 1*b*, the second distal-end portion 12*b* of the core shaft 12 is tapered in such a manner as to narrow from a side thereof having the proximal-end recessed portion 110 toward a side thereof having the distal-end recessed portion 100. That is, a gap D1 between the distal end 40*a* of the protective film 40 and the second distal-end portion 12*b* of the core shaft 12 is larger than a gap D2 between the proximal end 40*b* of the protective film 40 and the second distal-end portion 12*b* of the core shaft 12 (D1>D2). Therefore, the second distal-end portion 12*b* of the core shaft 12 comes into contact with the protective film 40 not over the entirety of the protective film 40 but only at the proximal end 40*b* of the protective film 40. Compared with the pusher guide wire 1, the frictional resistance generated between the protective film 40 and the stent 10 when the operator rotates the core shaft 12 is further reduced, and the damage to the stent 10 is further prevented. Furthermore, since the rotation of the core shaft 12 is transmitted to the distal-end tip 16 via the joining member 30 functioning as a distal-end stopper and the distal-end coil member 14, the transmissibility of rotation of the pusher guide wire 1*b* is further improved. Consequently, the position where the stent 10 is to be released is more easily adjustable.

To position the distal-end outlet 24 of the catheter 2 at the target site, the pusher guide wire 1, 1*a*, or 1*b* may be placed in the catheter 2 (as illustrated in FIG. 1A or 3A) in advance, and the catheter 2 and the pusher guide wire 1, 1*a*, or 1*b* may be delivered together to the target site. Alternatively, after the catheter 2 is solely positioned at the target site in advance, the pusher guide wire 1, 1*a*, or 1*b* may be inserted into the catheter 2 from the proximal-end inlet 22 of the catheter 2.

To summarize, in the pusher guide wire 1, the protective film 40 is suspended with respect to the core shaft 12 with the distal end 40*a* thereof being fitted in the distal-end recessed portion 100 and the proximal end 40*b* thereof being fitted in the proximal-end recessed portion 110. Hence, the frictional resistance generated between the protective film 40 and the stent 10 when the core shaft 12 is rotated is reduced. Thus, the protective film 40 is prevented from coming off the core shaft 12, the stent 10 is prevented from being damaged, and the transmissibility of rotation of the pusher guide wire 1 is improved. Consequently, the position where the stent 10 is to be released is easily adjustable.

What is claimed is:

1. A pusher guide wire that is configured to deliver a stent to a target site, the pusher guide wire comprising:
    a core shaft;
    a protective film that is provided around a portion of the core shaft and that is slidable in a longitudinal direction of the core shaft;
    a distal-end holder that is joined to the core shaft and that is configured to prevent the protective film from moving toward a distal end of the core shaft; and
    a proximal-end holder that is joined to the core shaft and that is configured to prevent the protective film from moving toward a proximal end side of the core shaft, wherein:
        a distal end of the protective film is disposed between the core shaft and the distal-end holder so that the distal end of the protective film is covered by the distal-end holder, and a proximal end of the protective film is disposed between the core shaft and the proximal-end holder so that the proximal end of the protective film is covered by the proximal-end holder, and
        the protective film does not rotate together with the core shaft when the core shaft is rotated.

2. The pusher guide wire according to claim 1, further comprising:
    a distal-end coil member that is wound around the core shaft and that extends from a distal end of the core shaft to a position located proximally of the distal end of the protective film; and
    a distal-end stopper that joins the core shaft to the distal-end coil member at a position located distally of the distal end of the protective film,
    wherein the distal-end holder includes a proximal-end portion of the distal-end coil member and the distal-end stopper.

3. The pusher guide wire according to claim 2, further comprising:
    a proximal-end coil member that is wound around the core shaft and that extends from a position located proximally of the proximal end of the protective film to a position located distally of the proximal end of the protective film; and
    a proximal-end stopper that joins the core shaft to the proximal-end coil member at a position located proximally of the proximal end of the protective film,
    wherein the proximal-end holder includes a distal-end portion of the proximal-end coil member and the proximal-end stopper.

4. The pusher guide wire according to claim 2, wherein:
    the core shaft narrows from the proximal-end holder toward the distal-end holder, and
    a gap between the distal end of the protective film and the core shaft is larger than a gap between the proximal end of the protective film and the core shaft.

5. The pusher guide wire according to claim 2, wherein the proximal-end holder is configured as a pusher portion for delivering the stent to the target site.

6. The pusher guide wire according to claim 1, further comprising:
    a proximal-end coil member that is wound around the core shaft and that extends from a position located proximally of the proximal end of the protective film to a position located distally of the proximal end of the protective film; and
    a proximal-end stopper configured to join the core shaft to the proximal-end coil member at a position located proximally of the proximal end of the protective film,
    wherein the proximal-end holder includes a distal-end portion of the proximal-end coil member and the proximal-end stopper.

7. The pusher guide wire according to claim 6, wherein:
    the core shaft narrows from the proximal-end the proximal end holder toward the distal-end holder, and
    a gap between the distal end of the protective film and the core shaft is larger than a gap between the proximal end of the protective film and the core shaft.

8. The pusher guide wire according to claim 6, wherein the proximal-end holder is configured as a pusher portion for delivering the stent to the target site.

9. The pusher guide wire according to claim 1, wherein:
    the core shaft narrows from the proximal-end holder toward the distal-end holder, and
    a gap between the distal end of the protective film and the core shaft is larger than a gap between the proximal end of the protective film and the core shaft.

10. The pusher guide wire according to claim 9, wherein the proximal-end holder is configured as a pusher portion for delivering the stent to the target site.

11. The pusher guide wire according to claim 1, wherein the proximal-end holder is configured as a pusher portion for delivering the stent to the target site.

12. The pusher guide wire according to claim 1, wherein the protective film is made of resin.

13. A pusher guide wire that is configured to deliver a stent to a target site, the pusher guide wire comprising:
    a core shaft;
    a protective film that is provided around a portion of the core shaft and that is slidable in a longitudinal direction of the core shaft;
    a distal-end holder that is joined to the core shaft and that is configured to prevent the protective film from moving toward a distal end of the core shaft;
    a proximal-end holder that is joined to the core shaft and that is configured to prevent the protective film from moving toward a proximal end side of the core shaft; and
    a proximal-end coil member that is wound around the core shaft and that extends from a position located proximally of a proximal end of the protective film to a position located distally of the proximal end of the protective film,
    wherein:
        a distal end of the protective film is covered by the distal-end holder, and the proximal end of the protective film is covered by the proximal-end holder, and
        the protective film does not rotate together with the core shaft when the core shaft is rotated.

14. The pusher guide wire according to claim 13, further comprising a distal-end coil member that is wound around the core shaft and that extends from a distal end of the core shaft to a position located proximally of the distal end of the protective film.

15. The pusher guide wire according to claim 14, further comprising:
a distal-end stopper that joins the core shaft to the distal-end coil member at a position located distally of the distal end of the protective film; and
a proximal-end stopper that joins the core shaft to the proximal-end coil member at a position located proximally of the proximal end of the protective film,
wherein:
the distal-end holder includes a proximal-end portion of the distal-end coil member and the distal-end stopper, and
the proximal-end holder includes a distal-end portion of the proximal-end coil member and the proximal-end stopper.

16. The pusher guide wire according to claim 13, wherein:
the core shaft narrows from the proximal-end holder toward the distal-end holder, and
a gap between the distal end of the protective film and the core shaft is larger than a gap between the proximal end of the protective film and the core shaft.

17. The pusher guide wire according to claim 13, wherein the proximal-end holder is configured as a pusher portion for delivering the stent to the target site.

18. The pusher guide wire according to claim 13, wherein the protective film is made of resin.

* * * * *